United States Patent [19]

Davis et al.

[11] Patent Number: 4,690,817

[45] Date of Patent: Sep. 1, 1987

[54] QUATERNARY NITROGEN CONTAINING POLYVINYL ALCOHOL POLYMERS FOR USE IN SKIN CONDITIONING, COSMETIC AND PHARMACEUTICAL FORMULATIONS

[75] Inventors: Ronald I. Davis; Charalambos J. Phalangas; George R. Titus, all of Wilmington, Del.

[73] Assignee: ICI Americas Inc., Wilmington, Del.

[21] Appl. No.: 747,239

[22] Filed: Jun. 21, 1985

Related U.S. Application Data

[62] Division of Ser. No. 540,041, Oct. 7, 1983, abandoned.

[51] Int. Cl.$^4$ .......................... A61K 7/06; A61K 7/08;
A61K 7/021; A61K 7/44
[52] U.S. Cl. .......................................... 424/70; 8/405;
8/406; 252/106; 252/107; 424/DIG. 12;
424/47; 424/59; 424/60; 424/61; 424/63;
424/64; 424/66; 424/68; 424/69; 424/73;
424/78; 514/844; 514/847; 514/969
[58] Field of Search .................... 424/47, 70, 60, 61,
424/66, 63, 73; 514/844; 525/56, 58, 60, 61, 375

[56] References Cited

U.S. PATENT DOCUMENTS

| | | | |
|---|---|---|---|
| 2,676,166 | 4/1954 | Webers et al. | 260/85.7 |
| 2,887,469 | 5/1959 | Unrih et al. | 260/77.5 |
| 2,972,606 | 2/1961 | Hartman et al. | 260/91.3 |
| 3,117,951 | 1/1964 | Itoli et al. | 260/91.3 |
| 3,121,607 | 2/1964 | Ohno et al. | 8/115.5 |
| 3,147,233 | 1/1964 | Mendelsohn | 260/29.6 |
| 3,338,883 | 8/1967 | Tesdro et al. | 260/212 |
| 3,348,997 | 10/1967 | Lagally et al. | 162/164 |
| 3,684,784 | 8/1972 | Marze | 260/80.3 N |
| 4,070,530 | 1/1978 | Hobbs | 526/7 |
| 4,182,804 | 1/1980 | Serboli et al. | 525/56 |

*Primary Examiner*—Dale R. Ore
*Attorney, Agent, or Firm*—Richard A. Rowe

[57] ABSTRACT

Polyvinyl alcohol polymers having pendant cationic quaternary nitrogen containing groups provide for a film forming moisture barrier in skin conditioning lotions, ointments, cosmetic conditioning treatments and pharmaceutical formulations.

5 Claims, No Drawings

QUATERNARY NITROGEN CONTAINING POLYVINYL ALCOHOL POLYMERS FOR USE IN SKIN CONDITIONING, COSMETIC AND PHARMACEUTICAL FORMULATIONS

This is a divisional of co-pending application Ser. No. 06/540,041 filed on 10/07/83, now abandoned.

The invention is directed to skin conditioning polymers which when applied to skin form thin films which aid in reducing moisture loss. The invention relates in general to film forming polyvinyl alcohol polymer derivatives and specifically to those having certain cationic quaternary nitrogen containing pendant groups. Of particular interest are polymers having a polyvinyl alcohol backbone or base chain with pendant substituent quaternary ammonium groups attached through oxygen linkages to the chain and spaced at random along the base chain. As a result of the presence of these quaternary ammonium groups in the polymer, thin film coatings on animal skin penetrate the outer layers of the skin to provide sufficient adhesive properties while remaining sufficiently elastomeric to avoid discomfort after drying. While the thin films act as a partially impenetrable barrier to prevent loss of moisture by evaporation they also behave as moisture retainers through the possible formation of hydrates at the quaternary ammonium sites and by inclusion of water molecules through hydrogen bonding on the hydrophilic polymer matrix. In general the compositions are made by treating readily available polyvinyl alcohol polymers with hydroxy reactive compounds containing quaternized ammonium groups linked thereto.

It is an object of the invention to provide for a quaternary nitrogen containing polyvinyl alcohol polymer base chain (having a number average molecular weight of at least 2,000 and preferably up to about 200,000 and higher when unmodified) and a random distribution of a multiplicity of oxy-linked pendant groups having the general formula:

$$-R-N^+R_1R_2R_3A^-$$

wherein
R is alkylene, substituted alkylene preferably hydroxyalkylene, or acylene of formula weight ranging from 14 to about 3,000,
$R_1$, $R_2$, $R_3$ are alkyl or arylalkyl radicals having 1-20 carbon atoms which may be the same or different,
$A^-$ is an anion,
such that the total nitrogen content in the resin polymer ranges from 0.01%–7.0% by weight. Another object is to provide for a preferred process for the synthesis of such compositions. It is still another object to provide for aqueous solutions containing 0.1–30% by weight of these polymers which are useful in skin conditioning lotions, ointments, cosmetic and pharmaceutical formulations for application to hair, skin and nails. Another object is to provide for a film forming polymer which also performs as a dispersant for particulates in such formulations.

R in the above formula may be selected from alkyl groups such as methylene, ethylene, propylene, butylene, pentylene, hexylene, ethylhexylene, dodecylene, tetradecylene, hexadecylene, octadecylene, and substituted alkyl groups such as hydroxypropylene, hydroxybutylene, acetyl, propionyl, butyryl, octadecanoyl, and octadecenoyl and their equivalents.

$R_1$, $R_2$, and $R_3$ may be selected from the alkyl groups such as methyl, ethyl, propyl, butyl, pentyl, hexyl, octyl, decyl, dodecyl, tridecyl, tetradecyl, hexadecyl, octadecyl, octadecenyl, phenyl, and benzyl and their equivalents.

$A^-$ may be selected from a large number of anions such as chloride, bromide iodide, hydroxide, lower alkylsulfate (1-6 carbon atoms), tetrafluoroborate, nitrate and perchlorate to name a few.

The quaternary nitrogen containing polyvinyl alcohol polymer compositions of the invention may be represented by a typical polymer segment having the following idealized structural formula:

$$-[(-CH_2CHORN^+R_1R_2R_3A^-)(-CH_2CHOH-)_m(CH_2CHORN^+R_1R_2R_3A^-)]_n-$$

where
n = 20–3000, and
m = 0–600, and
R, $R_1$, $R_2$, $R_3$, and $A^-$ are the same as described above.

Illustrative of the types of numerous pendant quaternary groups linked by oxygen as randomly distributed units in the polyvinyl alcohol base chain may be given as follows:

$$-CH_2CH(OH)CH_2N^+(CH_3)_3Cl^- \quad (1)$$

$$-(CH_2CH[CH_2N^+(CH_3)_3Cl^-]O)_nCH_2CH(OH)CH_2N^+(CH_3)_3Cl^- \; n=1-20 \quad (2)$$

$$-(C=O)CH_2N^+(CH_2CH_3)_3Br^- \quad (3)$$

$$-CH_2CH(OH)CH_2N^+(CH_3)_2(CH_2Ph)Cl^- \quad (4)$$

$$-CH_2CH_2N^+(CH_3)(CH_2CH_3)(CH_2Ph)CH_3SO_4^- \quad (5)$$

where Ph = phenyl.

While the above structures serve to illustrate the types of pendant quaternary ammonium groups which can be added to the polyvinyl alcohol base chain it is apparent to one skilled in the art that many other arrangements of similar chemical structure can be easily incorporated. It has been found that each of the above types of groups used alone or in combination with one or more of the others as a substituent on the polyvinyl alcohol base chain yields the desired combination of products having useful moisture barrier properties especially when the nitrogen content of the final product ranges from 0.01%–7% and preferably 0.01–3% by weight. Depending on the type of radical attached to the nitrogen of the quaternary group the effective range of the nitrogen content could be even more specific. It has been found for example that when the $R_1$, $R_2$, $R_3$, in the above general formulas are all methyl radicals the effective nitrogen content may range from 0.1–3% by weight.

While many techniques have been employed in the art to add substituent quaternary groups to vary polymer charge four preferred methods for attaching the substituent groups to polyvinyl alcohol involve the reaction of the hydroxy groups of polyvinyl alcohol with an epoxy (oxirane) group or a halohydrin group in aqueous solution, or a low molecular weight alkyl alcohol ester of the substituent in a dipolar aprotic solution or an acid halide in either a dipolar aprotic solvent or a two phase system in the presence of base catalyst or acid catalyst when appropriate.

While a number of methods may be utilized for the preparation of the PVA derivatives described in this invention, the use of non-aqueous solvents such as dimethyl formamide or similar polar materials is possible, but generally these solvents must be thoroughly removed from the final product. The use of aqueous solvents or mixed aqueous systems is preferable but, in this case, yields must be optimized because of competitive reactions of the quaternary ammonium compound with water as well as PVA hydroxyls in the presence of catalyst. Improved yields can be obtained by increasing the PVA concentration in water, adding the oxirane compound as a concentrate and reducing to a minimum the amount of base used to catalyze the addition reaction. Salt formed during the reaction is preferentially removed from the final product, since it may have a deleterious effect on the skin moisture barrier properties and its formulaton. It has also been found that the pH of the derivatized PVA may affect the skin moisture barrier properties as well as the substantivity to skin. It is generally desirable to work in a pH range between 2-10 preferably from 5-9.

The product can be obtained in a dry form by precipitation, filtering, drying and grinding. The precipitation is accomplished by adding the reaction mixture to a nonsolvent such as acetone, methanol, ethanol and the like. The product also finds use in the form of the aqueous solution or suspension which can preferably be obtained by dialyzing the reaction mass to free it from salts and low molecular weight unreacted intermediates. To obtain a better understanding of the preparative techniques found to be most satisfactory attention is drawn to the following generalized and specific preparations which are intended to illustrate but not limit the invention and wherein all proportions mentioned are based on weight unless otherwise specified.

GENERAL PREPARATION I

A flask equipped with a water cooled condenser, mechanical stirrer and thermometer is charged with polyvinyl alcohol and distilled water. The polyvinyl alcohol (PVA) which is generally a commercially available product prepared by hydrolysis of polyvinyl acetate may have from 0 to 25% residual acetate groups, preferably from 2 to 15% and the number average molecular weight may range from 2,000 to 200,000 and higher and preferably from 25,000 to 150,000. In addition, and for the purpose of this invention, a polyvinyl alcohol base chain may include up to 25% by weight of another comonomer such as vinyl pyrolidone, acrylic and methacrylic acids and esters thereof. The aqueous slurry is heated to 80°-90° C. and held for 1 hour or until the polyvinyl alcohol is completely dispersed or solvated. A catalytic amount of aqueous base such as alkali hydroxide such as sodium or potassium hydroxide is then added and the solution cooled to 40°-90° C. At this point 2,3-epoxypropyltrialkylammonium halide, either in aqueous solution or crystalline form, may be added incrementally or all at once. This reagent is typically used in 0.003-1.0 mol ratio preferably from 0.10-0.3 mol per mol of hydroxyl group on the polyvinyl alcohol base chain. The entire solution is then stirred for an additional period typically 4 hours at 60° C. after which the solid product may be recovered.

Recovery is accomplished by one of two general techniques. The solution can be poured into a polymer non-solvent to precipitate solid product from aqueous solution. Alternatively the solution may be dialyzed through a semiporous membrane and the purified aqueous polymer used as obtained or precipitated out.

The precipitation is preferably accomplished either in acetone or in methanol affording yields up to 90% or better by weight after drying. Depending on reaction conditions the precipitated products have a nitrogen content in the range of 0.01-7%.

In the purification by dialysis the reaction mixture is freed from all species below a certain molecular weight. Two methods may be used one a static and one dynamic. In the static method the reaction mixture is placed inside a commercial semi-porous dialysis tube and the tubes are submerged in distilled water typically for periods of 12 to 48 hours. The contents of the tubes are then recovered and the product may be used as is. In the dynamic system a pressure pump is used to move water from the reaction mixture through a semi-porous membrane. The water carries out any inorganics and low molecular weight organics. The resulting concentrated product stream is then collected.

GENERAL PREPARATION II

A flask equipped as described in General Preparation I is charged with polyvinyl alcohol and distilled water. The aqueous slurry is heated to 80°-90° C. and held for one hour or until the polymer is completely solvated. A catalytic amount of aqueous alkaline hydroxide such as sodium or potassium hydroxide is added and the pot cooled to 60°-65° C. At this point, (chlorohydroxypropyl)trimethylammonium halide, either in aqueous solution or crystalline form, is added either incrementally or all at once. This reagent is typically used in 0.003-1.0 mole ratio preferably from 0.10-0.5 mole per mole of hydroxyl group on the polyvinyl alcohol base chain. The entire solution is then stirred at 40°-90° C. for an additional period, typically four hours. The product is then recovered by one of the methods described in General Preparation I.

GENERAL PREPARATION III

In preparing quaternary ammonium groups linked to the polyvinyl alcohol base chain through ester linkages it is preferred to prepare them using a transesterification technique. In a typical reaction a four-neck one liter round bottom flask equipped with a thermometer, mechanical stirrer, water cooled condenser and a nitrogen sparger is charged with polyvinyl alcohol as described in the above General Preparation I, dimethylformamide, a trialkylalkoxycarbonyl ammonium halide, and a small amount of a transition metal salt as catalyst as manganese acetate for example. The entire dispersion is then heated to a temperature of 100°-110° C. for 2 to 24 hours preferably 3 to 6 hours. Nitrogen is used as a carrier gas to remove the alcohol formed during the esterification reaction. The solution is then cooled to ambient temperature and poured into a polymer nonsolvent such as for example methanol, ethanol or acetone. The resulting precipitate is collected by filtration, washed, shredded mechanically and dried under vacuum to afford a nearly white product with a desired nitrogen content.

GENERAL PREPARATION IV

A flask equipped as described in General Preparation I is charged with polyvinyl alcohol and distilled water. The aqueous slurry is heated to 80°-90° C. and held for one hour or until the polymer is completely dispersed or solvated. A catalytic amount of an acid such as sulfuric acid or aluminum hydrosilicate or any proton acid or Lewis acid is added and the pot cooled to 40°–90° C. At this point, 2,3-epoxypropyltrialkylammonium halide may be added incrementally or all at once. This reagent is typically used in 0.003–1.0 mole ratio preferably from 0.1–0.3 mol per mol of hydroxyl group on the polyvinyl alcohol base chain. The entire solution is then stirred for an additional period typically 4 hours at 60° C. after which the solid product may be recovered by one of the methods described in General Preparation I.

The following examples and preparations serve to illustrate but not limit the invention. All proportions used refer to parts by weight unless otherwise specified.

PREPARATION A (Chlorohydroxypropyl)trimethylammonium chloride

A one-liter flask equipped with dropping funnel, mechanical stirrer, thermometer and condenser was charged with epichlorohydrin (95 grams, 1.02 mol) and placed in an isothermal bath at 18° C. Aqueous trimethylamine (238.7 grams, 25% by weight, 1.01 mol) was then added dropwise over a 3 hour period maintaining the temperature below 25° C. when the addition was complete the solution was allowed to stir overnight at ambient temperature.

EXAMPLE 1

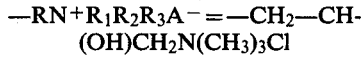

A flask equipped as described in General Preparation I was charged with 44 grams polyvinyl alcohol (commercially available) having a molecular weight of 126,000 (98% hydrolyzed—2% acetate) and 400 milliliters of distilled water. The resulting slurry was heated to 85° C. and held for 1 hour. The polymer dissolved completely to afford a pale yellow transparent solution. Potassium hydroxide (3.0 gram, 0.11 mol) in water (30 milliliters) was then added and the solution cooled to 60° C. Aqueous (chlorohydroxypropyl)trimethylammonium chloride (78 milliliters of 48% by weight aqueous solution prepared according to Preparation A), was then added all at once and the entire solution was heated to 60°–65° C. for 4 additional hours. The warm solution was poured with stirring into acetone (2.0 liters) and allowed to stand. 63.5 grams of colorless solid precipitate was collected by filtration shredded mechanically and dried under vacuum. The nitrogen content of the product was 2.15% by weight wherein the value for (m) in the above general formula segment is approximately 21.

PREPARATION B

Crystalline 2,3-epoxypropyltrimethylammonium chloride

A one-liter flask equipped with gas sparger, mechanical stirrer, thermometer and an aqueous acid trap was charged with epichlorohydrin (55.2 grams, 6.0 mol) and placed in an isothermal bath at 19° C. Trimethylamine gas (119.5 grams, 2.0 mol) was then sparged into the epichlorohydrin over a period of 3 hours. The temperature was maintained below 23° C. The solution was stirred for an additional 30 minutes and the precipitate collected by filtration. The crystalline product was washed with diethylether and vacuum dried to afford 262.2 grams of 2,3-epoxypropyltrimethylammonium chloride.

EXAMPLE 2

The procedure of Example 1 was repeated exactly except that pure crystalline 2,3-epoxypropyltrimethylammonium chloride (15.2 grams, 0.10 mol) was added in place of the aqueous solution. The mixture was then stirred for an additional 5.5 hours at 60° C. and recovered from acetone as described. The nitrogen content of the final product was 1.12% by weight wherein the value for (m) is approximately 28.

EXAMPLE 3

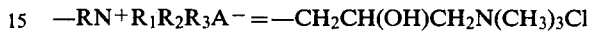

The procedure of Example 1 was reproduced except that the amount of aqueous 2,3-epoxypropyltrimethylammonium chloride was 56.2 milliliters of 48% solution and the warm aqueous polymer was recovered by precipitation in methanol (2.0 liters). The solid collected was shredded mechanically dried under vacuum and milled to a fine powder. The yield was 49.9 grams and the nitrogen content was 0.22% by weight wherein the value for (m) in the general formula segment is approximately 282.

EXAMPLE 4

The procedure of Example 3 was reproduced with the exception that the aqueous reaction mixture was cooled to ambient temperature and placed in a commercially available dialysis tube. The semi-pourous membrane in the dialysis tube retains all molecules with molecular weights greater than 8,000. The tubes were placed in water (4 liters) and allowed to stand. The bath water was changed ever 6–8 hours over a 36 hour period. The tubes were then recovered and the aqueous polymer solution inside was tested for moisture barrier properties.

EXAMPLE 5

The procedure of Example 3 was reproduced with the exception that recovery was accomplished by precipitation from acetone (1.5 liters). The scale was slightly reduced to 38.0 grams polyvinyl alcohol and 49 milliliters of 48% aqueous epoxide solution. The yield was 63.5 grams and the nitrogen content was 2.63% by weight wherein the value for (m) in the general formula segment is approximately 15.

PREPARATION C

Preparation of 2,3-epoxypropyltrimethylammonium bromide

A flask equipped with a sparger, mechanical stirrer, thermometer and efficiency condenser was charged with acetone (500 milliliters) at ambient temperature. Trimethylamine (58 grams, 0.98 mol) was charged into the solution. The pot was cooled to 10° C. and epibromohydrin (137 grams, 1.0 mol) was added dropwise over a 1 hour period. The resultant cloudy solution was allowed to slowly rise to ambient temperature and stand for 60 hours. Precipitate was collected by filtration washed with acetone (60 milliliters) and dried yielding a colorless crystalline product (179.4 grams, 94%).

EXAMPLE 6

—RN+R₁R₂R₃A⁻=—CH₂CH(OH)CH₂N(CH₃)₃Br

A flask equipped as described in General Preparation I was charged with polyvinyl alcohol (44.0 grams), (98% hydrolyzed, number average molecular weight equals 126,000) and 500 milliliters water. The slurry was warmed to 70° C. and potassium hydroxide (3.0 grams) was added. The pot was stirred an additional 30 minutes and 2,3-epoxypropyltrimethylammonium bromide (49.0 grams, 0.25 moles) was added through a powder funnel. This solution was stirred for 16 hours at 80° C. The solution was then poured into acetone (1500 milliliters) and the precipitate was collected by filtration, shredded, washed and dried. The pale brown solid powder which resulted had a nitrogen content of 2.10% by weight wherein the value for (m) in the general formula segment is approximately 19.

EXAMPLE 7

—RN+R₁R₂R₃A⁻=—CH₂CH(OH)CH₂N+(CH₃)₃Cl

A flask equipped as described in General Preparation I was charged with polyvinyl alcohol (44.0 grams), (100% hydrolyzed, number average molecular weight equals 86,000), 200 milliliters distilled water and 3 grams potassium hydroxide. The pot was heated to 60° C. an aqueous (chlorohydroxypropyl)trimethylammonium chloride (320 milliliters, 48% aqueous solution as prepared in Preparation A) was added. Heating was continued for an additional 24 hours and recovery was accomplished by precipitation from acetone. After collection washing and drying the nitrogen content was 0.72% wherein the value for (m) in the general formula segment is approximately 80.

EXAMPLE 8

—RN+R₁R₂R₃A⁻=—CH₂CH(OH)CH₂N+(CH₃)₃Cl

A flask equipped as described in General Preparation I was charged with polyvinyl alcohol (88.0 grams), (98.5% hydrolyzed, having a molecular weight of 25,000) and 800 milliliters of water. The reaction was carried out exactly as described in Example 2 using crystalline 2,3-epoxypropyltrimethylammonium chloride (79.6 grams). Recovery was accomplished by precipitation in acetone. The nitrogen content was 1.01% by weight wherein the value for (m) in the general formula segment is approximately 84.

EXAMPLE 9

—RN+R₁R₂R₃A⁻=—COCH₂N+(CH₃)₂(CH₂Ph)Cl

A flask equipped as described in General Preparation II was charged with polyvinyl alcohol (44.0 grams), (100% hydrolyzed, molecular weight 86,000), 500 milliliters dimethylformamide, 5.5 grams maganese acetate, and benzyldimethylethoxycarbonylmethyl ammonium chloride (51.0 grams, 0.25 mole). A nitrogen stream was passed through the solution as was heated to 125° C. and held for 6 hours. The resulting solution was poured into acetone (1500 milliliters) while hot. The precipitate was collected by filtration, shredded mechanically, washed again with polymer non-solvent and dried. The product was found to have a chloride content of 4.10% by weight and a calculated nitrogen content of 1.62% wherein the value for (m) in the general formula segment is approximately 28.

EXAMPLE 10

—RN+R₁R₂R₃A⁻=—COCH₂N+(CH₃)₂(CH₂Ph)Cl

The process of Example 9 was repeated with polyvinyl alcohol (98% hydrolyzed having molecular weight of 126,000). The chloride content of the product was 4.41% by weight and the calculated nitrogen content was 1.72% wherein the value for (m) in the general formula segment is approximately 25.

EXAMPLE 11

—RN+R₁R₂R₃A⁻=—CH₂CH(OH)CH₂N+(CH₃)₃Cl

Polyvinyl alcohol (44.0 g, MW=126,000, 98% hydrolyzed) was stirred in water (400 ml) and warmed to 85°–90° C. The solution was cooled to 80° C. and aqueous potassium hydroxide (5.6 g in 30 ml H₂O) was added. This solution was cooled over 30 minutes to 60° C. and (3-chloro-2-hydroxypropyl)trimethylammonium chloride (18.8 g, 0.10 mol) was added all at once. The pH at this time was 7.3. The product was recovered by dialysis through a semi-porous membrane as previously described. The nitrogen content was 0.15% which corresponds to idealized formula with m=415.

EXAMPLE 12

—RN+R₁R₂R₃A⁻=—CH₂CH(OH)CH₂N+(CH₃)₃Cl

Polyvinyl alcohol (22.0 g), (MW=126,000, 98% hydrolyzed) was stirred in water (210 ml) and warmed to 85° C. over 45 minutes. Potassium hydroxide (1.5 g in 10 ml H₂O) was then added and the solution cooled to 60° C. Crystalline 2,3-epoxypropyltrimethylammonium chloride (75.8 g, 0.50 mol) was added and the entire solution held at 60° C. for 4 hours. The product was then recovered by precipitation from acetone, filtration and drying to afford 102 grams of white powder. The nitrogen content was 5.96% or 88% of theoretical, and wherein (m) has a value of approximately 2.0.

EXAMPLE 13

—RN+R₁R₂R₃A⁻=—CH₂CH(OH)CH₂N+(CH₃)₃Cl

Polyvinyl alcohol (44.0 g), (MW=126,000, 98% hydrolyzed) was stirred in water (400 ml) and warmed to 85° C. over 30 minutes. The solution was cooled to 80° C. and Potassium hydroxide (3.0 g in 20 ml H₂O) was added. The entire solution was cooled to 60° C. over 45 minutes and 2,3-epoxypropyltrimethylammonium chloride (37.9 g in 100 ml H₂O) was added dropwise over 30 minutes. The solution was stirred at 60° C. for 3 additional hours and the product recovered by precipitation from acetone. The reaction afforded 50.4 grams of white solid with a nitrogen content of 2.92% or 71% of theoretical, and wherein (m) has a value of approximately 13.

MOISTURE BARRIER TEST ON PAPER

While the modified polyvinyl alcohol polymers of the invention are best tested for retentivity, substantivity and moisture barrier film forming properties on living animal skin an indication of their effectiveness as a moisture barrier can be obtained by testing on filter paper. In the test results listed in the following Table 1 a 2.5 inch circle of number 1 Whatman filter paper was treated with aqueous solutions containing from 5–10% by weight of the modified polymer as described in the examples to obtain a polymer film deposit amounting to about 0.1 gram when dried at room temperature. The test is carried out by taking about 2 grams of aqueous solution of the modified polymer and dropping it over a water wet circle of filter paper from one side. The saturated paper is permitted to dry overnight at room temperature and weighed. Depending on the concentration of solution the procedure may be repeated until the weight pickup is about 0.1 gram so that each filter paper is treated with substantially an equal amount of polymer. The dry paper is sealed over the opening of a test cell containing 100 grams of water and permitted to stand for 100 hours in a constant humidity and temperature room at 70° F. at 40% relative humidity. The weight of water passing through the paper under these conditions is measured by weighing the amount of water remaining in the test cell. Each test employs a control cell containing the identical paper having no polymer treatment. Considering the weight loss through untreated paper as 100 the test results which are listed as percentage reduction in evaporation of water are calculated from the water remaining in the cell. The paper test results provide a rough indication of effectiveness as a moisture barrier for further testing on animal skin.

TABLE 1

| Example | % Reduction in Evaporation |
|---|---|
| Control (unmodified PVA) | 40-50 |
| 1 | 55 |
| 2 | 36 |
| 3 | 61 |
| 4 | 58 |
| 5 | 33 |
| 6 | 59 |
| 7 | 46 |
| 8 | — |
| 9 | 40 |
| 10 | 51 |

In-vitro tests on animal skins having 1, 3 and 5 weight percent of the modified polyvinyl alcohol polymers of this invention indicate comparable results with regard to water vapor transmission on Neo-Natal Rat Stratum Corneum as shown in the results listed in Table 2.

TABLE 2

| Water Vapor Transmission (5% polymer solution on neo-natal rat stratum corneum) | |
|---|---|
| Sample | % Reduction |
| Control | 66.7 |
| Example 1 | 55.6 |
| Example 7 | 77.8 |
| Example 8 | 55.6 |

The effect of polymer coatings having 5% modified PVA polymers on the elasticity of pig skin is shown in Table 3.

TABLE 3

| Elasticity of pig skin treated with 5% polymer solution | |
|---|---|
| Sample | Elasticity |
| Control | 7.8 ± 2.6 |
| Example 1 | 8.8 ± 2.0 |
| Example 7 | 11.4 ± 2.0 |
| Example 8 | −1.6 ± 0.8 |

Compares skin elasticity (petroleum jelly produces maximum elasticity—approximately 28 units)

The use of unmodified polyvinyl alcohol polymer in film forming ointment bases and barrier creams for use in protecting the skin against the action of external irritants has met with only limited success (J. B. Ward and G. J. Sperandio, "American Perfumer and Cosmetics" Volume 79, pages 53–55 (1964)). Film forming creams are difficult to produce with polyvinyl alcohol because they are either very difficult to formulate because of their poor mixing characteristics or they form poor films. Lotions and creams made with polyvinyl alcohol in general lack elegance, that is, the in-vitro films made from ointments and lotions containing about 15% polyvinyl alcohol are either slow drying, become greasy and tacky and eventually leave a film which is hard and leathery. Furthermore, good PVA moisture barrier films usually are very hard to remove from the skin because they are difficult to remove with soap and water.

The problems associated with employing unmodified PVA in film forming bases are substantially overcome by the compositions of this invention in that they are easily dispersible in water are compatible with typical lotion formulations, and when applied to the surface of the skin, they dry quickly to form an elastic, smooth pellicle which retains its integrity over long periods of time and is easily removed with soap and water. Tests for pharmaceutical elegance is accomplished by applying typical moisture barrier lotion formulas to the back of the hand and making observations with respect to ease of application, feel on the skin, time of drying, durability of the film, ease of removal and a host of subjective factors. In most instances, the formulations evaluated do not adversely effect the film forming characteristics of the modified polyvinyl alcohol compositions of this invention. The aqueous moisture barrier compositions of the invention generally have a lotion consistency and may be in the form of oil-in-water or water-in-oil emulsions with the former being preferred because of their more pleasing cosmetic properties. The lotions are preferably made by first preparing the oil phase then preparing the water phase and thereafter adding the water phase to the oil phase. Usually the aqueous phase is heated to a temperature of about 70° to about 80° C. and then added slowly with stirring to the oil phase which is heated to about the same temperature.

The oil phase components may contain a variety of materials including emulsifiers, emollients, oils, waxes, perfumes, lanolins, polyalkylenes, stearols and the like.

Water phase components may contain many different materials which include humectants, modified PVA moisture barrier components of the invention, proteins and polypeptides, preservatives, alkaline agents, thickening agents, perfumes, stabilizers and antiseptics.

The lotions and ointments of the invention contain as an essential ingredient from 0.1–15% by weight and preferably from 0.5–5% by weight of the above described modified polyvinyl alcohol polymers of the invention. They may be added as aqueous dispersions containing 0.1–30% by weight of modified PVA or as dry powder.

The lotions may contain an emulsifier in an amount of from about 0.05 to about 8% and preferably from about 0.25 to about 5% to emulsify the oil components. Typical emulsifiers are selected from the group consisting of polyethoxylated fatty acids having less than about 30 mols of ethylene oxide per mol of fatty acid, ethyoxylated esters, unethoxylated sugar esters, polyoxyethylene fatty ether phosphates, fatty acid amides, phospholipids, polypropoxylated fatty ethers, acyllactates, polyethoxylated polyoxypropylene glycols, polypropoxylated polyoxyethylene glycols, polyoxyethylene, polyoxypropylene ethylene diamines, soaps and mixtures thereof.

Examples of such emulsifiers include polyoxyethylene (8) stearate, myristyl ethoxy (3) myristate, myristyl ethoxy (3) palmitate, methyl glucose sesquistearate, sucrose distearate, sucrose laurate, sorbitan monolaurate, polyoxyethylene (3) oleyl ether phosphate, polyoxyethylene (10) oleyl ether phosphate, lauric diethenyl amide, stearic monoethyl amide, lecithin, lanoline alcohol propoxylates, sodium stearoyl-2-lactate, calcium stearoyl-2-lactate, and the Pluoronics ® offered by BASF Wyandotte. Soaps such as alkaline metal or triethanolamine salts of long chain fatty acids which include sodium stearate, triethanolamine stearate and similar salts of lanolin fatty acids. A preferred emulsifier is polyoxyethylene (21) stearyl ether.

The lotion formulations may contain an emollient material in an amount ranging from 0.2 to 25% and more often 1 to 8% by weight. One function of the emollient is to ensure that the modified polyvinyl alcohol polymer is classified sufficiently to allow it to be in a film-like state on the surface of the skin. Typical emollients are selected from the group consisting of fatty alcohols, esters having fewer than about 24 carbon atoms (for example, isopropylpalmitate), branch chain esters having greater than about 24 total carbon atoms (for example, cetearyl octonate), squalane, liquid or solid paraffins, mixtures of fatty acids and squalane, mixtures of fatty acids and liquid or solid paraffins and mixtures thereof. Typical alcohols and fatty acids which are useful include those having from 12 to 22 carbon atoms such as cetyl alcohol, myristyl alcohol, stearyl alcohol, stearic acid and palmitic acid. Paraffins include, for example, mineral oil, petrolatum and paraffin wax.

The lotions and ointments are particularly stable and effective when adjusted to a pH of 6–8.

The following formulations will serve to demonstrate but not limit the formulations containing the modified polyvinyl alcohol film forming moisture barrier polymer of the invention. Typical lotions contain 0.1–5.0% of the above described modified PVA polymers, 2–5% of a fatty alcohol, and 2–5% emulsifier in an aqueous emulsion.

EXAMPLE A

A portion of the aqueous solution prepared according to Example 4 containing 0.5 grams of modified PVA polymer was diluted with water and added to an aqueous solution containing 2.4 grams cetyl alcohol, 1.6 grams stearyl alcohol and 3.0 grams of polyoxyethylene (21) stearyl ether (BRIJ ® 721 surfactant by ICI Americas Inc.). Additional water was added to bring the water concentration to 92.5%. After stirring for about five minutes at 75° C. the emulsion is permitted to cool to room temperature and stored. The lotion was tested subjectively for cosmetic elegance by applying the product to the back of the hand and arm. It was determined to have smooth, silky feel, drying time of less than 15 minutes and a film durability in excess of two days. Residual films and lotions are easily removed from the skin with soap and water.

As mentioned above the polymers of the invention had advantageous cosmetic properties that permit them to be used in preparing cosmetic formulations either as ready to use compositions or concentrates which have to be diluted before use. Therefore, the cosmetic formula may contain the modified polyvinyl alcohol polymers in concentrations ranging from 0.01–15% by weight. The solution of these polymers are particularly useful when they are applied to hair, either alone or with other active substances during a treatment such as shampooing, dyeing, setting, blow drying, permanent waving, etc. They may improve notably the quality of the hair. When employed in hair treatment they facilitate untangling of wet hair and do not remain on dry hair as a sticky residue. In some instances they are expected to give dry hair additional life, a soft feel, a glossy appearance and resistance to tangling.

Hair treating formulations containing dilute aqueous, alcohol or dilute alcohol solutions of the modified polyvinyl alcohol polymer can be employed. Furthermore, they may be employed as creams, lotions, gels or as aerosol sprays. They may be used in combination with perfumes, dyes, preserving agents, sequestering agents, thickening agents, emulsifying agents, etc.

EXAMPLE B

A typical hair rinse formulation containing 5 grams of the modified polymer of Example 8, 7 grams cetyl alcohol, 3 grams of a linear polyoxyethylenated $C_{10}$–$C_{18}$ fatty alcohol, 2 grams of a casein derivative, 0.5 grams tetradecyltrimethylammonium chloride and 82.5 grams of water and a minor amount of hair dye can be used to treat hair having improved looks and anti-static properties.

EXAMPLE C

A typical oxidation hair dye solution containing a 2.5 gram of the modified polymer of Example 9, 10 grams benzyl alcohol, 20 grams oleic acid, 3 grams polyoxyethylene (30), oleo cetyl alcohol, 7 grams oleic diethanolamide 7.5 grams 2 octyldodecanol, 2.5 grams triethanolamine lauric sulfate, 10 grams ethanol, 18 milliliters aqueous ammonium, 1 gram n,n-bis(2-hydroxyethanol)paraphenylenediamine, 0.4 grams resorcin, 0.15 grams m-aminophenol, 0.4 grams alphanaphthol, 0.1 grams hydroquinone, 0.24 grams ethylene diamine tetracetic acid, 1 milliliter sodium bisulfite, and water sufficient to make 100 grams is a typical ammonia oil composition for use as an oxidation hair dye when 130 grams of the solution is mixed with 30 grams of hydrogen peroxide bleach. After hair is treated with the material and allowed to stand for 30–40 minutes and thereafter rerinsed the hair is expected to untangle easily and have a silky touch.

The modified polyvinyl alcohol compositions of the invention may be employed to improve the elegance and stability of personal care products such as liquid and bar soaps, shaving creams, bath products, antiperspirants, sunscreens, cleansing creams and as a suspending agent for insoluble pigments and pharmaceutical actives. Improvement is generally realized when from 0.5–5% by weight of the compositions of this invention are employed in conventional formulations as hereinafter exemplified.

EXAMPLE D

Roll-On Antiperspirant

| Ingredient | % W/W |
| --- | --- |
| Example 3 | 4.0 |
| polyoxyethylene (21) stearylether | 0.76 |

-continued

| Ingredient | % W/W |
| --- | --- |
| polyoxyethylene (2) stearylether | 3.24 |
| water (deionized) | 34.76 |
| Dowicil 200 ®, Dow Chemical | 0.1 |
| Al Zr tetrachlorohydrex-Gly, Rezol 36G, Reheis | 57.14 |

EXAMPLE E

Aerosol Shave Cream

| Ingredient | % W/W |
| --- | --- |
| Example 3 | 5.0 |
| Cetyl alcohol | 4.3 |
| polyoxyethylene (21) stearylether | 2.2 |
| sorbic acid | .17 |
| water | 74.9 |
| fragrance | .08 |
| water | 13.35 |

EXAMPLE F

Oil-in-Water Sunscreen Lotion

| Ingredient | W/W % |
| --- | --- |
| mineral oil | 18.8 |
| cetyl alcohol | 5.0 |
| Arlocel 60 ® emulsifier | 2.5 |
| Tween 60 ® emulsifier | 7.5 |
| Amyl para-dimethylaminobenzoic-acid | 1.2 |
| Example 4 | 2.0 |
| water | 63.0 |
| Preservative | q.s. |

EXAMPLE G

Water-in-Oil Pigmented Makeup

| Ingredient | W/W % |
| --- | --- |
| Mineral Oil | 10 |
| Beeswax | 1.5 |
| Cevesin wax | 1.0 |
| Arlacel 186 ® emulsifier | 3.2 |
| Sorbo ® sorbitol | 28.8 |
| TiO2 and other pigments | 20.0 |
| water | 33.5 |

-continued

| Ingredient | W/W % |
| --- | --- |
| Example 6 | 2.0 |

EXAMPLE H

Calamine Lotion

| | |
| --- | --- |
| Calamine | 80 gms |
| Zinc Oxide | 80 gms |
| glycerine | 20 mls |
| bentonite magma | 250 mls |
| calcium hydroxide (concentrated aqueous sol.) | 950 mls |
| Example 1 | 50 gms |

What is claimed is:

1. In an improved aqueous hair and skin conditioning composition comprising an oil phase, a water phase, and 0.05% to about 8% of an emulsifier wherein the improvement comprising reducing moisture loss with an aqueous solution containing 0.1 to 30% by weight of a quaternary nitrogen modified polyvinylalcohol polymer having a molecular weight ranging from at least 2,000 up to about 200,000 and which comprises a polyvinyl alcohol having oxygen-linked pendant groups of the formula $-R-NR_1R_2R_3A-$ wherein R is selected from the group consisting of alkylene, hydroxy substituted alkylene and an acylene radical of formula weight ranging from 14 to about 3000, $R_1$, $R_2$ and $R_3$ are selected from the group consisting of alkyl and arylalkyl having 1-20 carbon atoms, $A^-$, is an anion, said polymers having a total nitrogen ranging from 0.01-7% by weight.

2. An aqueous skin conditioning composition of claim 1 comprising 0.1-10% by weight of said modified polyvinyl alcohol polymer, 2-5% by weight of an emulsifier and 2-5% by weight of an emollient.

3. A composition of claim 1 wherein $R_1$, $R_2$ and $R_3$ are methyl groups and the nitrogen content ranges from 0.01-3% by weight.

4. An aqueous hair conditioning composition of claim 1 comprising 0.1-10% by weight of said modified polyvinyl alcohol polymer, 2-5% by weight of an emulsifier and 2-5% by weight of an emollient.

5. A composition of claim 1 wherein $R_1$, $R_2$ and $R_3$ are methyl groups and the nitrogen content ranges from 0.01-3% by weight.

* * * * *